US006518483B1

(12) United States Patent
Bruce et al.

(10) Patent No.: US 6,518,483 B1
(45) Date of Patent: Feb. 11, 2003

(54) ROOT-PREFERRED PROMOTERS AND THEIR USE

(75) Inventors: Wesley B. Bruce, Urbandale, IA (US); Lynne E. Sims, Polk City, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/444,905

(22) Filed: Nov. 22, 1999

Related U.S. Application Data

(60) Provisional application No. 60/109,721, filed on Nov. 24, 1998.

(51) Int. Cl.[7] .......................... A01H 5/00; C07H 21/04; C12N 5/14; C12N 15/11; C12N 15/82
(52) U.S. Cl. ...................... 800/287; 800/298; 536/24.1; 435/320.1; 435/419; 435/468
(58) Field of Search .............................. 435/320.1, 419, 435/468; 536/24.1; 800/287, 298

(56) References Cited

FOREIGN PATENT DOCUMENTS

| WO | WO94/04196 A1 | 3/1994 |
| WO | WO94/04562 A1 | 3/1994 |
| WO | WO97/44448 A1 | 11/1997 |

OTHER PUBLICATIONS

P. Benfey et al, "The Cauliflower Mosaic Virus 35S Promoter" Combinatorial Regulation of Transcription in Plants, Nov. 1990, Science vol. 250, pp. 959–966.*
Kim et al, "A 20 nucleotide upstream element is essential for the nopaline synthase (nos) promter activity", 1994, Plant Molecular Biology vol. 24, pp. 105–117.*
Lu, Guihua and Bruce, Wesley B. A Novel Cis–Acting Element Conferring Root–Preferred Gene Expression in Maize, *J. Plant Physiol.*, 2000, pp. 277–283, vol. 156.
Lincoln et al. (1994) "A Knotted1–Like Homeobox Gene In Arabidopsis Is Expressed In The Vegetative Meristem and Dramatically Alters Leaf Morphology When Overexpressed In Transgenic Plants", *The Plant Cell* 6(*12*):1859–1876.
Serikawa et al. (1996) "Three Knotted1–Like Homeobox Genes In Arabidopsis ", *Plant Molecular Biology* 32:673–683.
Ma et al. (1994) "Identification of a Homeobox–Containing Gene With Enhanced Expression During Soybean (*Glycine max*L. ) Somatic Embryo Development", *Plant Molecular Biology* 24:465–473.
Long et al. (1996) "A Member of the Knotted Class of Homeodomain Proteins Encoded by the STM Gene of Arabidopsis", *Nature* 379:66–69.
Kerstetter et al. (1994) "Sequence Analysis and Expression Patterns Divide the Maize knotted1–like Homeobox Genes into Two Classes", *The Plant Cell* 6:1877–1887.

* cited by examiner

*Primary Examiner*—Amy J. Nelson
*Assistant Examiner*—Cynthia Collins
(74) *Attorney, Agent, or Firm*—Alston & Bird LLP

(57) ABSTRACT

The present invention provides compositions and methods for regulating expression of heterologous nucleotide sequences in a plant. Compositions include a novel nucleotide sequence for a root-preferred promoter for the gene encoding Knox1, a Kn1-like homeobox gene and sequences isolated therefrom. A method for expressing a heterologous nucleotide sequence in a plant using the promoter sequences disclosed herein is provided. The method comprises stabling incorporating into the genome of a plant cell a nucleotide sequence operably linked to the root-preferred promoter of the present invention and regenerating a stably transformed plant that expresses the nucleotide sequence.

22 Claims, 4 Drawing Sheets

ROOT-PREFERRED PROMOTERS AND THEIR USE

CROSS-REFERENCE TO RELATED APPLICATIONS

This Application claims the benefit of U.S. Provisional Application No. 60/109,721, filed Nov. 24, 1998.

FIELD OF THE INVENTION

The present invention relates to the field of plant molecular biology, more particularly to regulation of gene expression in plants.

BACKGROUND OF THE INVENTION

Expression of heterologous DNA sequences in a plant host is dependent upon the presence of an operably linked promoter that is functional within the plant host. Choice of the promoter sequence will determine when and where within the organism the heterologous DNA sequence is expressed. Where expression in specific tissues or organs is desired, tissue-preferred promoters may be used. Where gene expression in response to a stimulus is desired, inducible promoters are the regulatory element of choice. In contrast, where continuous expression is desired throughout the cells of a plant, constitutive promoters are utilized. Additional regulatory sequences upstream and/or downstream from the core promoter sequence may be included in expression constructs of transformation vectors to bring about varying levels of expression of heterologous nucleotide sequences in a transgenic plant.

Frequently it is desirable to express a DNA sequence in particular tissues or organs of a plant. For example, increased resistance of a plant to infection by soil- and air-borne pathogens might be accomplished by genetic manipulation of the plant's genome to comprise a tissue-preferred promoter operably linked to a heterologous pathogen-resistance gene such that pathogen-resistance proteins are produced in the desired plant tissue.

Alternatively, it might be desirable to inhibit expression of a native DNA sequence within a plant's tissues to achieve a desired phenotype. In this case, such inhibition might be accomplished with transformation of the plant to comprise a tissue-preferred promoter operably linked to an antisense nucleotide sequence, such that expression of the antisense sequence produces an RNA transcript that interferes with translation of the iRNA of the native DNA sequence.

Thus far, the regulation of gene expression in plant roots has not been adequately studied despite the root's importance to plant development. To some degree this is attributable to a lack of readily available, root-specific biochemical functions whose genes may be cloned, studied, and manipulated. Genetically altering plants through the use of genetic engineering techniques and thus producing a plant with useful traits requires the availability of a variety of promoters. An accumulation of promoters would enable the investigator to design recombinant DNA molecules that are capable of being expressed at desired levels and cellular locales. Therefore, a collection of tissue-preferred promoters would allow for a new trait to be expressed in the desired tissue.

Thus, isolation and characterization of tissue-preferred, particularly root-preferred, promoters that can serve as regulatory regions for expression of heterologous nucleotide sequences of interest in a tissue-preferred manner are needed for genetic manipulation of plants.

SUMMARY OF THE INVENTION

Compositions and methods for regulating expression of heterologous nucleotide sequences in a plant are provided. Compositions comprise novel promoter sequences that initiate transcription in a root-preferred manner. More particularly, a transcriptional initiation region isolated from the plant gene Knox1 is provided. Further compositions of the invention comprise the nucleotide sequence set forth in SEQ ID NO:1, a fragment of the nucleotide sequence set forth in SEQ ID NO:1 comprising at least 20 nucleotides, and the nucleotide sequence deposited as Patent Deposit No. 98917. The compositions of the invention further comprise nucleotide sequences having at least 70% identity to the sequence set forth in SEQ ID NO:1 or a fragment thereof, and nucleotide sequences that hybridized under stringent conditions to any one of the above mentioned sequences.

Compositions of the present invention also include an expression cassette comprising a promoter, operably linked to a nucleotide sequence of interest, wherein said promoter is capable of driving expression of said nucleotide sequence in a plant cell and said promoter comprises the nucleotide sequences of the present invention. The invention further provides an expression vector comprising the above mentioned expression cassette.

Compositions further include a plant or a plant cell having stably incorporated into their genomes an expression cassette comprising a promoter operably linked to a nucleotide sequence, wherein said promoter is capable driving expression of said nucleotide sequence in a plant cell and said promoter comprises a nucleotide sequence of the present invention. Additionally, compositions include the seed of such plants.

Methods of the invention comprise a means to express a nucleotide sequence in a plant, said method comprising, stably incorporating into the genome of a plant cell an expression cassette comprising a promoter operably linked to a nucleotide sequence, wherein said promoter is capable of initiating transcription of said nucleotide sequence in said plant cell and said promoter comprises a nucleotide sequence of the present invention.

DETAILED DESCRIPTION OF THE INVENTION

Figure 1:
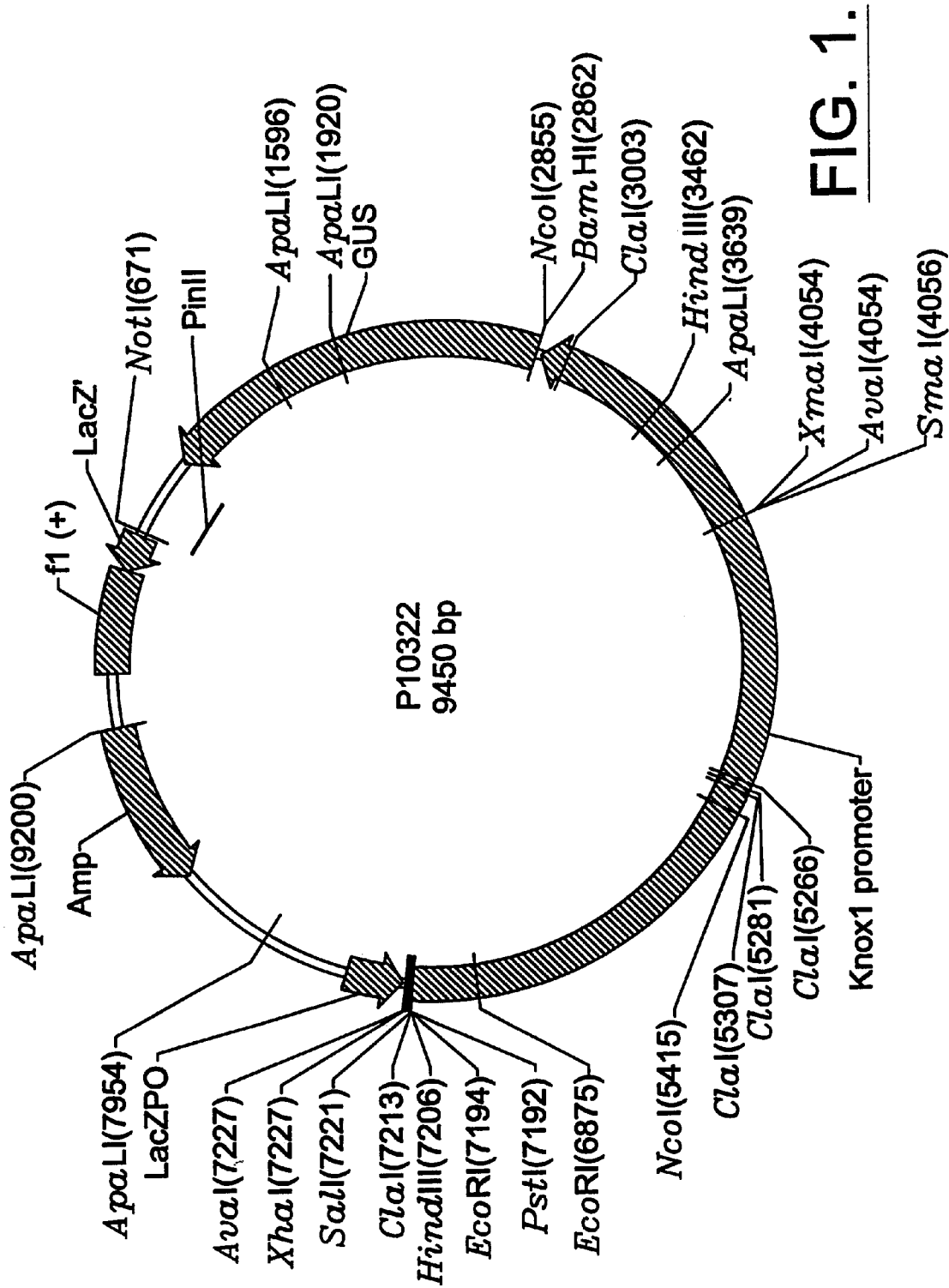
FIG. 1 schematically illustrates the plasmid vector P10322 comprising the GUS gene operably linked to the Knox1 promoter.

The compositions of the present invention comprise novel nucleotide sequences for plant promoters, particularly a "root-preferred" promoter for the Knox1 gene, a Kn1-like homeobox gene, more particularly, the maize Knox1 promoter. In particular, the present invention provides for an isolated nucleic acid molecule comprising the nucleotide sequences set for forth in SEQ ID NO:1, and DNA sequences deposited in a bacterial host as Patent Deposit No. 98917, on Oct. 7, 1998, and fragments and variants thereof.

A plasmid containing the nucleotide sequences of the invention were deposited with the Patent Depository of the American Type Culture Collection (ATCC), Manassas, Va., and assigned Patent Deposit No. 98917. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

The Knox1 gene encodes a homeodomain protein that involved in the transcriptional control of developmentally regulated genes. Homeodomain proteins contain conserved regions known as "homeobox domains" consisting of a helix-turn-helix motif that has a DNA binding function. The maize Knox1 gene is preferentially expressed in maize root tissue, although low levels of expression may occur in other tissues as well. See, for example, Vollbrecht et al. (1991) *Nature* 350:241–243 and Kerstetter et al. (1994) *The Plant Cell* 6:1877–1887, herein incorporated by reference.

The knox1 promoter sequences of the present invention direct expression of operably linked nucleotide sequences in a root-preferred manner. Therefore, the knox1 promoter sequences find use in the root-preferred expression of an operably linked nucleotide sequence of interest.

Furthermore, the level of knox1 directed expression in the root is increased in high yielding maize hybrids planted at high density. Hence, the knox1 promoter sequences find use in improving plant growth and/or crop yields under higher planting densities by regulating the expression of genes which improve the plant's response to stresses induced under high density growth conditions. By "high density growth conditions" or "high density" is intended increasing the number of plants per area by about 50%, 100%, 200%, 300%, 400%, 600%, 800% or greater compared to the optimal growth density conditions of the plant. Alternatively, "high density" encompasses an increase in the number of plants per area from about 50% to about 200%, about 200% to about 400%, about 400% to about 600%, or about 600% to about 800% or greater compared to the optimal growth density conditions of the plant.

Fragments and variants of the disclosed nucleotide sequence are also encompassed by the present invention. By "fragment" is intended a portion of the nucleotide sequence. Fragments of a nucleotide sequence may retain biological activity and hence encompass fragments capable of driving root-preferred expression of an operably linked nucleotide sequence. Biologically active fragments of the knox1 promoter can also retain the ability to increase transcription of operably linked nucleotide sequences under high-density growth conditions. Alternatively, fragments of a nucleotide sequence that are useful as hybridization probes generally do not retain biological activity. Thus, fragments of a nucleotide sequence may range from at least about 20 nucleotides, about 50 nucleotides, about 100 nucleotides, and up to the full-length nucleotide sequence of the invention.

Thus, a fragment of a knox1 promoter nucleotide sequence may encode a biologically active portion of the knox1 promoter or it may be a fragment that can be used as a hybridization probe or PCR primer using methods disclosed below. A biologically active portion of a knox1 promoter can be prepared by isolating a portion of one of the knox1 promoter nucleotide sequences of the invention, and assessing the activity of that portion of the knox1 promoter. Nucleic acid molecules that are fragments of a knox1 promoter nucleotide sequence comprise at least 16, 20, 50, 75, 100, 150, 200, 250, 300, 350, 400, 450, 500, 550, 600, 650, 700, 800, 900, 1,000, 1,100, 1,200, 1,300, or 1,400, 1,600, 1,800, 2,000, 2,200, 2,500, 3,000, 3,200, 3,500, 4,000, 4,300 nucleotides, or up to the number of nucleotides present in a full-length knox1 promoter nucleotide sequence disclosed herein (for example, 4315 nucleotides for SEQ ID NO:1).

By "variants" is intended substantially similar sequences. For nucleotide sequences naturally occurring variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis. Generally, variants of a particular nucleotide sequence of the invention will have at least 40%, 50%, 60%, 70%, generally at least 75%, 80%, 85%, preferably about 90% to 95% or more, and more preferably about 98% or more sequence identity to that particular nucleotide sequence as determined by sequence alignment programs described elsewhere herein using default parameters. Biologically active variants are also encompassed by the present invention. Biologically active variants include, for example, the native promoter sequence of the invention having one or more nucleotide substitutions, deletions or insertions. Promoter activity may be measured by using techniques such as Northern blot analysis, reporter activity measurements taken from transcriptional fusions, and the like. See, for example, Sambrook et al. (1989) *Molecular Cloning: A Laboratory Manual* (2d ed., Cold Spring Harbor Laboratory Press, Cold Spring Harbor, N.Y.), herein incorporated by reference.

Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein.

Variant nucleotide sequences also encompass sequences derived from a mutagenic and recombinogenic procedure such as DNA shuffling. With such a procedure, one or more different knox1 promoter sequences can be manipulated to create a new knox1 promoter possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

The nucleotide sequences of the invention can be used to isolate corresponding sequences from other organisms, particularly other plants. In this manner, methods such as PCR, hybridization, and the like can be used to identify such sequences based on their sequence homology to the sequence set forth herein. Sequences isolated based on their sequence identity to the entire knox1 promoter sequence set forth herein or to fragments thereof are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the knox1 promoter sequence of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire knox1 sequence disclosed herein, or one or more portions thereof, may be used as a probe capable of specifically hybridizing to corresponding knox1 promoter sequences. To achieve specific hybridization under a variety of conditions, such probes include sequences that are unique among knox1 promoter sequences and are preferably at least about 10 nucleotides in length, and most preferably at least about 20 nucleotides in length. Such probes may be used to amplify corresponding knox1 promoter sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1 989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284: $T_m=81.5°$ C.+16.6 (log M)+0.41 (%GC)–0.61 (% form)– 500/L; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that have promoter activity and which hybridize under stringent conditions to the knox1 promoter sequence disclosed herein, or to fragments thereof, are encompassed by the present invention. Such sequences will be at least 40% to 50% homologous, about 60% to 70% homologous, and even about 75%, 80%, 85%, 90%, 95% to 98% homologous or more with the disclosed sequence. That is, the sequence identity of sequences may range, sharing at least 40% to 50%, about 60% to 70%, and even about 75%, 80%, 85%, 90%, 95% to 98% or more sequence identity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence, for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Preferred, non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch (1970) *J. Mol. Biol.* 48:443–453; the search-for-similarity-method of Pearson and Lipman (1988) *Proc. Natl. Acad. Sci.* 85:2444–2448; the algorithm of Karlin and Altschul (1990) *Proc. Natl. Acad. Sci. USA* 872264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237–244 (1988), Higgins et al. (1989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al. (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See http://www.ncbi.nlm.nih.gov. Alignment may also be performed manually by inspection.

For purposes of the present invention, comparison of nucleotide or protein sequences for determination of percent sequence identity to the knox1 promoter sequences disclosed herein is preferably made using the Blast program (Version 2.0 or later) with its default parameters any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol Biol.* 48:443–453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The coding sequence expressed by the promoters of the invention may be used to vary the phenotype of a plant. Various changes in phenotype are of interest including modifying expression of a gene in a plant root, altering a plant's pathogen or insect defense mechanism, increasing the plant's tolerance to herbicides, altering root development to respond to environmental stress, and the like. These results can be achieved by providing expression of heterologous or increased expression of endogenous products in plants. Alternatively, the results can be achieved by providing for a reduction of expression of one or more endogenous products, particularly enzymes, transporters, or cofactors, or affecting nutrient uptake in the plant. These changes result in a change in phenotype of the transformed plant.

General categories of genes of interest for the present invention include, for example, those genes involved in information, such as Zinc fingers, those involved in communication, such as kinases, and those involved in housekeeping, such as heat shock proteins. More specific categories of transgenes, for example, include genes encoding important traits for agronomics, insect resistance, disease resistance, and herbicide resistance. It is recognized that any gene of interest can be operably linked to the promoter of the invention and expressed in plant roots.

Insect resistance genes may encode resistance to pests that have great yield drag such as rootworm, cutworm, European Corn Borer, and the like. Such genes include, for example *Bacillus thuringiensis* toxic protein genes (U.S. Pat. Nos. 5,366,892; 5,747,450; 5,737,514; 5,723,756; 5,593,881; Geiser et al. (1986) *Gene* 48:109); lectins (Van Damme et al. (1994) *Plant Mol. Biol.* 24:825); and the like.

Genes encoding disease resistance traits include detoxification genes, such as against fumonosin (U.S. patent application Ser. No. 08/484,815, filed Jun. 7, 1995); avirulence (avr) and disease resistance (R) genes (Jones et al. (1994) *Science* 266:789, Martin et al. (1993) *Science* 262:1432; Mindrinos et al. (1994) *Cell* 78:1089); and the like.

Herbicide resistance traits may be introduced into plants by genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS gene encodes resistance to the herbicide chlorsulfuron.

Exogenous products include plant enzymes and products as well as those from other sources including prokaryotes and other eukaryotes. Such products include enzymes, cofactors, hormones, and the like.

Examples of other applicable genes and their associated phenotype include the gene which encodes viral coat protein and/or RNA, or other viral or plant genes that confer viral resistance, genes that confer fungal resistance; genes that promote yield improvement; and genes that provide for resistance to stress, such as dehydration resulting from heat and salinity, toxic metal or trace elements, or the like.

In other embodiments of the present invention, the knox1 promoter sequences are operably linked to genes of interest that improve plant growth or increase crop yields under high plant density conditions. For example, the knox1 promoter may be operably linked to nucleotide sequences expressing agronomically important genes that result in improved primary or lateral root systems. Such genes include, but are not limited to, nutrient/water transporters and growth induces. Examples of such genes, include but are not limited to, maize plasma membrane $H^+$-ATPase (MHA2) (Frias et al. (1996) *Plant Cell* 8:1533–44); AKT1, a component of the potassium uptake apparatus in Arabidopisis, (Spalding et al. (1999) *J Gen Physiol* 113:909–18); RML genes which activate cell division cycle in the root apical cells (Cheng et al. (1995) *Plant Physiol* 108:881); maize glutamine synthetase genes, (Sukanya et al. (1994) *Plant Mol Biol* 26:1935–46) and hemoglobin (Duff et al. (1997) *J. Biol. Chem* 27:16749–16752, Arredondo-Peter et al. (1997) *Plant Physiol.* 115:1259–1266; Arredondo-Peter et al. (1997) *Plant Physiol* 114:493–500 and references sited therein). The knox1 promoter sequence may also be useful in expressing antisense nucleotide sequences of genes that that negatively affects root development under high planting density conditions.

The heterologous nucleotide sequence operably linked to the promoter disclosed herein may be an antisense sequence for a targeted gene. By "antisense DNA nucleotide sequence" is intended a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing to the endogenous messenger RNA (mRNA) produced by transcription of the DNA nucleotide sequence for the targeted gene. In this case, production of the native protein encoded by the targeted gene is inhibited to achieve a desired phenotypic response. Modifications of the antisense sequences may be made as long as the sequences hybridize to and interfere with expression of the corresponding mRNA. In this manner, antisense constructions having 70%, preferably 80%, more preferably 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used. Thus, the promoter sequences disclosed herein may be operably linked to antisense DNA sequences to reduce or inhibit expression of a native protein in the plant root.

By "promoter" or "transcriptional initiation region" is intended a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate. It is recognized that having identified the nucleotide sequences for the promoter regions disclosed herein, it is within the state of the art to isolate and identify further regulatory elements in the 5' untranslated region upstream from the particular promoter regions identified herein. Additionally, translational fusions may be provided. Such fusions include portions of the amino acid sequence. Thus the promoter regions disclosed herein are generally further defined by comprising upstream regulatory elements such as, those responsible for tissue and temporal expression of the coding sequence, enhancers and the like. In the same manner, the promoter elements, which enable expression in the desired tissue such as the root, can be identified isolated and used with other core promoters to confer root-preferred expression.

The regulatory sequences of the present invention, when operably linked to a heterologous nucleotide sequence of interest and stably incorporated into the plant genome drive "root-preferred" expression of the heterologous nucleotide sequence. By "root-preferred" is intended that expression of the heterologous nucleotide sequence is most abundant in the root. By root is intended any part of the root structure, including but not limited to, the root cap, apical meristem, protoderm, ground meristem, procambium, endodermis, cortex, vascular cortex, epidermis, and the like. While some level of expression of the heterologous nucleotide sequence may occur in other plant tissue types, expression occurs most abundantly in the root including primary, lateral, and adventitious roots.

By "heterologous nucleotide sequence" is intended a sequence that is not naturally occurring with the promoter sequence. While this nucleotide sequence is heterologous to the promoter sequence, it may be homologous, or native, or heterologous, or foreign, to the plant host.

The isolated promoter sequences of the present invention can be modified to provide for a range of expression levels of the heterologous nucleotide sequence. Thus, less than the entire promoter regions may be utilized and the ability to drive expression of the coding sequence retained. However, it is recognized that expression levels of the mRNA may be decreased with deletions of portions of the promoter sequences. Generally, at least about 20 nucleotides of an isolated promoter sequence will be used to drive expression of a nucleotide sequence.

It is recognized that to increase transcription levels enhancers may be utilized in combination with the promoter regions of the invention. Enhancers are nucleotide sequences that act to increase the expression of a promoter region. Enhancers are known in the art and include the SV40 enhancer region, the 35S enhancer element, and the like.

Modifications of the isolated promoter sequences of the present invention can provide for a range of expression of the heterologous nucleotide sequence. Thus, they may be modified to be weak promoters or strong promoters. Generally, by "weak promoter" is intended a promoter that drives expression of a coding sequence at a low level. By "low level" is intended at levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts.

It is recognized that the promoters of the invention thereof may be used with their native coding sequences to increase or decrease expression, thereby resulting in a change in phenotype of the transformed plant.

The nucleotide sequences for the root-preferred promoters disclosed in the present invention, as well as variants and fragments thereof, are useful in the genetic manipulation of any plant when operably linked with a heterologous nucleotide sequence whose expression is to be controlled to achieve a desired phenotypic response. By "operably linked" is intended the transcription of the heterologous nucleotide sequence is under the influence of the promoter sequence. By "operably linked" is also intended the joining of two nucleotide sequences such that the coding sequence of each DNA fragment remain in the proper reading frame. In this manner, the nucleotide sequences for the promoters of the invention may be provided in expression cassettes along with heterologous nucleotide sequences of interest for expression in the plant of interest, more particularly in the root of the plant.

Such expression cassettes will comprise a transcriptional initiation region comprising the promoter nucleotide sequences of the present invention, or variants or fragments thereof, operably linked to a heterologous nucleotide sequence whose expression is to be controlled by the root-preferred promoter disclosed herein. Such an expression cassette is provided with a plurality of restriction sites for insertion of the nucleotide sequence to be under the transcriptional regulation of the regulatory regions. The expression cassette may additionally contain selectable marker genes.

The expression cassette will include in the 5'-to-3' direction of transcription, a transcriptional and translational initiation region, a heterologous nucleotide sequence of interest, and a transcriptional and translational termination region functional in plants. The termination region may be native with the transcriptional initiation region comprising the promoter nucleotide sequence of the present invention, may be native with the DNA sequence of interest, or may be derived from another source. Convenient termination regions are available from the Ti-plasmid of *A. tumefaciens*, such as the octopine synthase and nopaline synthase termination regions. See also, Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. 1989) *Nucleic Acids Res.* 17:7891–7903; Joshi heterologous et al. (1987) *Nucleic Acid Res.* 15:9627–9639.

The expression cassette comprising the promoter sequence of the present invention operably linked to a heterologous nucleotide sequence may also contain at least one additional nucleotide sequence for a gene to be cotransformed into the organism. Alternatively, the additional sequence(s) can be provided on another expression cassette.

Where appropriate, the heterologous nucleotide sequence whose expression is to be under the control of the root-preferred promoter sequence of the present invention and any additional nucleotide sequence(s) may be optimized for increased expression in the transformed plant. That is, these nucleotide sequences can be synthesized using plant preferred codons for improved expression. Methods are available in the art for synthesizing plant-preferred nucleotide sequences. See, for example, U.S. Pat. Nos. 5,380,831 and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the heterologous nucleotide sequence may be adjusted to levels average for a given cellular host, as calculated by reference to known genes expressed in the host cell. When possible, the sequence is modified to avoid predicted hairpin secondary MRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Nat. Acad. Sci. USA* 86:6126–6130); potyvirus leaders, for example, TEV leader (Tobacco Etch Virus) (Allison et al. (1986)); MDMV leader (Maize Dwarf Mosaic Virus) (*Virology* 154:9–20); human immunoglobulin heavy-chain binding protein (BiP) (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) *Molecular Biology of RNA*, pages 237–256); and maize chlorotic mottle virus leader (MCMV) (Lommel et al. (1991) *Virology* 81:382–385). See also Della-Cioppa et al. (1987) *Plant Physiology* 84:965–968. Other methods known to enhance translation and/or MRNA stability can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, for example, transitions and transversions, may be involved.

Reporter genes or selectable marker genes may be included in the expression cassettes. Examples of suitable reporter genes known in the art can be found in, for example, Jefferson et al. (1991) in *Plant Molecular Biology Manual*, ed. Gelvin et al. (Kluwer Academic Publishers), pp. 1–33; DeWet et al. (1987) *Mol. Cell. Biol.* 7:725–737; Goff et al. (1990) *EMBO J.* 9:2517–2522; Kain et al. (1995) *Bio Techniques* 19:650–655; and Chiu et al. (1996) *Current Biology* 6:325–330.

Selectable marker genes for selection of transformed cells or tissues can include genes that confer antibiotic resistance or resistance to herbicides. Examples of suitable selectable marker genes include, but are not limited to, genes encoding resistance to chloramphenicol (Herrera Estrella et al. (1983) *EMBO J.* 2:987–992); methotrexate (Herrera Estrella et al. (1983) *Nature* 303:209–213; Meijer et al. (1991) *Plant Mol. Biol.* 16:807–820); hygromycin (Waldron et al. (1985) *Plant Mol. Biol.* 5:103–108; Zhijian et al. (1995) *Plant Science* 108:219–227); streptomycin (Jones et al. (1987) *Mol. Gen. Genet.* 210: 86–91); spectinomycin (Bretagne-Sagnard et al. (1996) *Transgenic Res.* 5:131–137); bleomycin (Hille et al. (1990) *Plant Mol. Biol.* 7:171–176); sulfonamide (Guerineau et al. (1990) *Plant Mol. Biol.* 15:127–136); bromoxynil (Stalker et al. (1988) *Science* 242:419–423); glyphosate (Shaw et al. (1986) *Science* 233:478–481); phosphinothricin (DeBlock et al. (1987) *EMBO J.* 6:2513–2518).

Other genes that could serve utility in the recovery of transgenic events but might not be required in the final product would include, but are not limited to, examples such as GUS (b-glucoronidase; Jefferson (1987) *Plant Mol. Biol. Rep.* 5:387), GFP (green florescence protein; Chalfie et al. (1994) *Science* 263:802), luciferase (Riggs et al. (1987)

*Nucleic Acid Res.* 15(19):8115 and Luehrsen et al. (1992) *Methods Enzymol.* 216:397–414) and the maize genes encoding for anthocyanin production (Ludwig et al. (1990) *Science* 247:449).

The expression cassette comprising the particular promoter sequence of the present invention operably linked to a nucleotide sequence of interest can be used to transform any plant. In this manner, genetically modified plants, plant cells, plant tissue, seed, root, and the like can be obtained.

Such plant species, including, but are not limited to, corn (*Zea mays*), Brassica sp. (e.g., *B. napus, B. rapa, B. juncea*), particularly those Brassica species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetim glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (Cofea spp.), coconut (*Cocos nucijera*), pineapple (*Ananas comosus*), citrus trees (Citrus spp.), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (Saccharum spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (Lathyrus spp.), and members of the genus Cucumis such as cucumber (*C. sativus*), cantaloupe (*C. cantalupensis*), and musk melon (*C. melo*). Ornamentals include azalea (Rhododendron spp.), hydrangea (*Macrophylla hydrangea*), hibiscus (*Hibiscus rosasanensis*), roses (Rosa spp.), tulips (Tulipa spp.), daffodils (Narcissus spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinusponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thujaplicata*) and Alaska yellow-cedar (*Chamaecyparis nootkatensis*). Preferably, plants of the present invention are crop plants (for example, corn, alfalfa, sunflower, Brassica, soybean, cotton, safflower, peanut, sorghum, wheat, millet, tobacco, etc.), more preferably corn and soybean plants, yet more preferably corn plants.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat No. 5,563,055), direct gene transfer (Paszkowski et al. (1984) *EMBO J*. 3:2717–2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin), and McCabe et al. (1988) *Biotechnology* 6:923–926). Also see Weissinger et al. (1988) *Ann. Rev. Genet.* 22:421–477, Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet*. 96:319–324 (soybean); Datta et al. (1990) *Biotechnology* 8:736–740 (rice); Klein et al. (1988) *Proc. Natl. Acad Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol*. 91:440–444 (maize); Fromm et al. (1990) *Biotechnology* 8:833–839 (maize); Hooykaas-Van Slogteren et al. (1984) *Nature* (London) 311:763–764; Bowen et al., U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, N.Y.), pp. 197–209 (pollen); Kaeppler et al. (1990) *Plant Cell Reports* 9:415–418 and Kaeppler et al. (1992) *Theor. Appl. Genet*. 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75: 407–413 (rice); Osjoda et al. (1996) *Nature Biotechnology* 14:745–750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having root-preferred expression of the desired phenotypic characteristic identified. Two or more generations may be grown to ensure that root-preferred expression of the desired phenotypic characteristic is stably maintained and inherited and then seeds harvested to ensure root-preferred expression of the desired phenotypic characteristic has been achieved.

The following examples are offered by way of illustration and not by way of limitation.

EXPERIMENTAL

The promoter region for the maize gene knox1 was isolated from maize plants. The sequence for the knox1 promoter is set forth in SEQ ID NO:1. The method for its isolation is described below.

EXAMPLE 1

Isolation of Promoter Sequences

One to three-week old *Zea mays* cv. B73 were grown in soil in the greenhouse. Whole root and whole leaf tissue were harvested and immediately frozen in liquid nitrogen. Total RNA was harvested using TriPure Reagent (Boehringer Mannheim, Indianapolis, Ind.) and the manufacturer's protocol. PolyA RNA was isolated from 1–3 mg total RNA using a magnetic-bead-poly dT method from Promega (Madison, Wis.). Exactly 4.2 μg and 6 μg of root and leaf polyA RNA, respectively, were denatured with a solution of 50% formamide, 6% formaldehyde, 0.5×MOPS and 0.01% Bromphenol Blue by heating the RNA mixtures at 65° C. for 15 minutes then placed on ice. The RNA was loaded on a 1.2% SeaKEM GTG agarose gel with 1×MOPS and 2% Formaldehyde and run at 70 volts for 2 hours. Using 20×SSC, the RNA gels were transferred overnight to a Nytran membrane using the Turboblot System (GIBCO BRL, Gaithersburg, Md.). Following blotting, the membranes were air dried and crosslinked with UV using a Stratalinker at a setting of 1200 microjoules (Stratagene, LaJolla, Calif.). The membranes were then prehybridized with 10 ml of 1×"Expresshyb" solution (Clontech, Palo Alto, Calif.) for 1 hour at 65° C. The 5' and 3' KNOX1 probes were radiolabeled using Redivue random priming labeling method from Amersham (UK) with $^{32}P$-α-dCTP and added to fresh 1×Expresshyb solution for hybridization to the membrane at 65° C. overnight. The membranes were washed two times with 2×SSC, 0.1% SDS for 10 minutes at room temperature. This was followed by a single stringent wash with 0.1×SSC, 0.1% SDS for 30 minutes at 50° C. The membranes were exposed to Kodak XAR X-ray film at –80° C. with DuPont Intensifier screen for 4 days. Endogenous transcripts from the maize knox1 gene were detected by Northern analysis. A strong knox1 mRNA band was observed in root but not in leaf tissues (data not shown).

EXAMPLE 2

Expression Data Using Promoter Sequences

Figure 2:
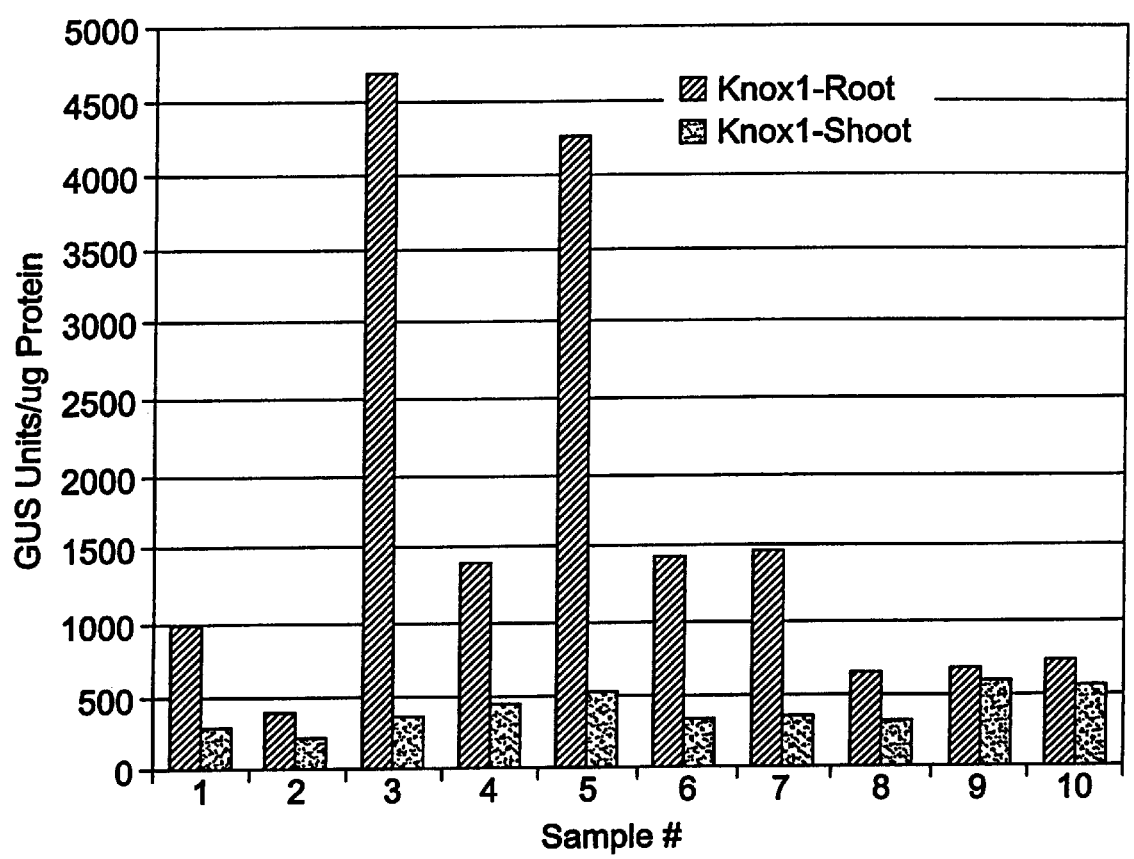
FIG. 2 shows transient expression levels of a Knox1::GUS DNA construct in root and shoot tissue from maize.

Nine (9) μg of PHP10322 (FIG. 1) plus 1 μg of Ubi::LUC to act as a standard control were precipitated onto tungsten particles and bombarded into 3-day old seedlings essentially as described in Tomes et al. Shoots and roots were harvested separately and measured for GUS activity using GUS Light Kit from Tropix (San Diego, Calif.) following the manufacturer's protocol. Protein assays were conducted with Bradford Protein Assay from BioRad (Hercules, Calif.) Emoryville kit. Results are shown in FIG. 2. The data show normalized GUS units as recorded on a Luminometer to soluble protein.

EXAMPLE 3

Transformation and Regeneration of Maize Callus

Figure 3:
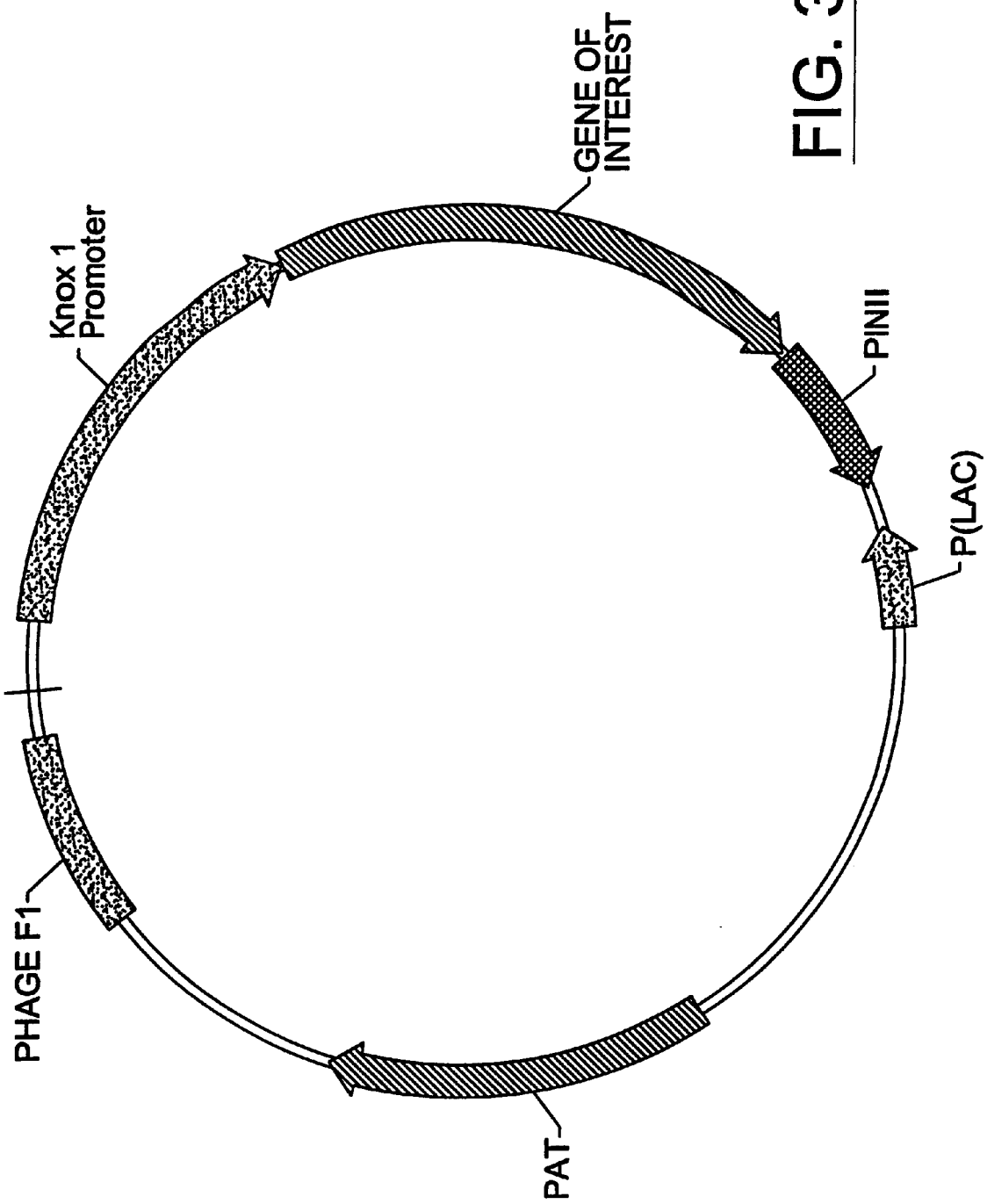
FIG. 3 schematically illustrates the plasmid vector comprising a gene of interest operably linked to a promoter of the invention.

Immature maize embryos from greenhouse donor plants are bombarded with a plasmid containing the knox1 promoter sequence operably linked to a nucleotide sequence of interest (FIG. 3). The plasmid further contains the selectable marker gene PAT (Wohlleben et al. (1988) *Gene* 70:25–37) that confers resistance to the herbicide Bialaphos. Transformation is performed as follows. All media recipes are listed below.

Preparation of Target Tissue

The ears are surface sterilized in 30% Chlorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

The plasmid vector shown in FIG. 3 is precipitated onto 1.1 μm (average diameter) tungsten pellets using a $CaCl_2$ precipitation procedure as follows:

100 μl prepared tungsten particles in water
10 μl (1 μg) DNA in TrisEDTA buffer (1 μg total)
100 μl 12.5 M $CaCl_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity, Plants are monitored and scored for the an altered phenotypic trait.

Bombardment and Culture Media

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos(both added after sterilizing the medium and cooling to room temperature).

Plant regeneration medium (288J) comprises 4.3 g/l MS salts (GIBCO 11117–074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I H₂O after adjusting to pH 5.6); 3.0 g/l Gelrite (added after bringing to volume with D-I H₂O); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117–074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I H₂O), 0.1 g/l myo-inositol, and 40.0 g/l sucrose (brought to volume with polished D-I H₂O after adjusting pH to 5.6); and 6 g/l bacto-agar (added after bringing to volume with polished D-I H₂O), sterilized and cooled to 60° C.

EXAMPLE 4

Expression of the Knox1 Gene Under High Density Growth Conditions

Figure 4:
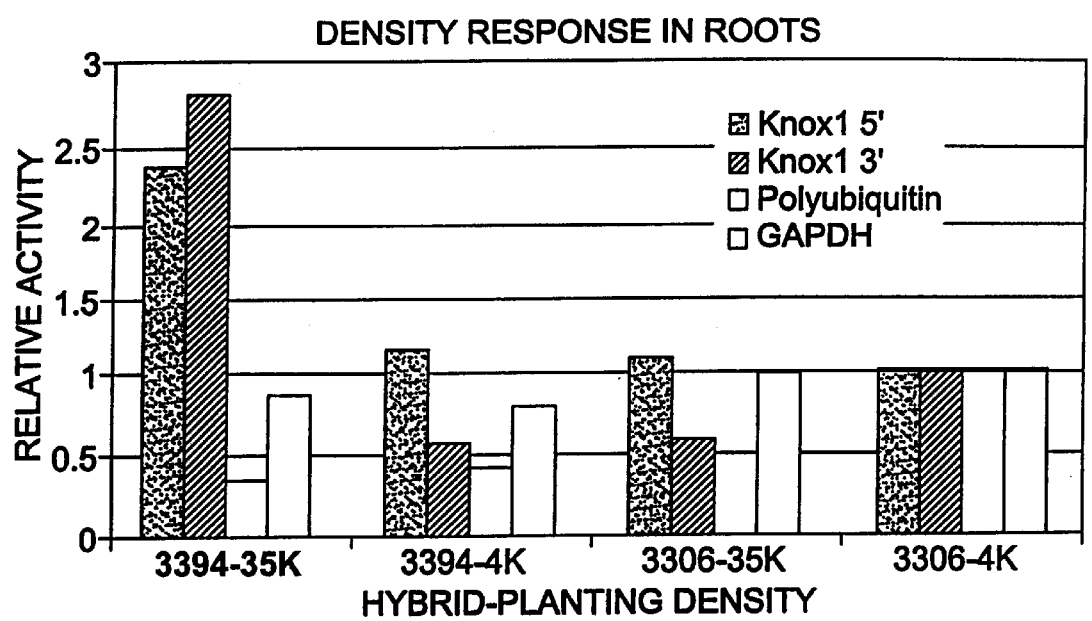
FIG. 4 shows that the knox1 gene is expressed in a high yielding hybrid maize strain in a density-response fashion.

Two maize hybrids, 3394 and 3306, were planted at high-density equivalents to 35,000 plant/acre. Half of each hybrid was thinned to an equivalent of 4,000 plants/acre. The 3394 hybrid yields very well at the high density relative to the 3306 hybrid. Root RNA was isolated using standard protocols from two developmental stages, V8 and V12-R1. The RNA was converted to a probe and applied onto the Affymetrix Genechip supplied for Pioneer's corn EST database using published protocols. The GeneChip includes representative oligos for 1501 Pioneer EST clones. Each gene is represented by 20 oliogs of perfect matches and 20 oligos of single base pair mismatch. Using Affymetrix methods for measuring gene expression levels, we determined that the knox1 gene is expressed in the high yielding hybrid in a density-response fashion. This suggests that the knox1 promoters may harbor promoter elements that stimulate expression in the appropriate hybrids under the high-density growth conditions. FIG. 4 depicts the relative mRNA levels for two parts of knox1 (5' and 3' end loaded on the GeneChip) and two controls, polyubiquitin and glyceraldehyde 3-phosphate dehydrogenase (GAPDH). The mRNA levels were normalized to the 3306 hybrid at 4K density planting for each gene. The knox1 gene was expressed 2–2.5 times higher in the 3394 hybrid at high planting densities that at low planting densities whereas the controls were regulated at similar levels in roots.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An isolated promoter that is capable of driving expression in a plant cell, wherein said promoter comprises the nucleotide sequence set forth in SEQ ID NO:1 and said promoter is capable of driving root-preferred expression of an operably linked nucleotide sequence.

2. An expression cassette comprising a promoter operably linked to a nucleotide sequence, wherein said promoter is capable of driving root-preferred expression of said nucleotide sequence, wherein said promoter comprises the nucleotide sequence set forth in SEQ ID NO:1.

3. An expression vector comprising the expression cassette of claim 2.

4. A plant having stably incorporated into its genome an expression cassette comprising a promoter operably linked to a nucleotide sequence, wherein said promoter is capable of driving root-preferred expression of said nucleotide sequence and said promoter comprises the nucleotide sequence set forth in SEQ ID NO:1.

5. The plant of claim 4, wherein said plant is a monocot.

6. The plant of claim 5, wherein said monocot is maize.

7. The plant of claim 4, wherein said plant is a dicot.

8. Seed of the plant of claim 4, said seed comprising said expression cassette.

9. A method for expressing a nucleotide sequence in a plant, said method comprising, stably incorporating into the genome of a plant cell an expression cassette comprising a promoter operably linked to a nucleotide sequence, wherein said promoter is capable of initiating transcription of said nucleotide sequence in a root-preferred manner and said promoter comprises the nucleotide sequence set forth in SEQ ID NO:1.

10. The method of claim 9, wherein said nucleotide sequence is selectively expressed in the root.

11. A plant cell having stably incorporated into its genome an expression cassette comprising a promoter operably linked to a nucleotide sequence, wherein said promoter is capable of initiating transcription of said nucleotide sequence in a root-preferred manner and said promoter comprises the nucleotide sequence set forth in SEQ ID NO:1.

12. The plant cell of claim 11, wherein said plant cell is from a monocotyledonous plant.

13. The plant cell of claim 12, wherein said plant cell is from maize.

14. The plant cell of claim 11, wherein said plant cell is from a dicotyledonous plant.

15. An isolated promoter that is capable of driving expression in a plant cell, wherein said promoter is the promoter deposited with the ATCC as Patent Deposit No. 98917 and said promoter is capable of driving root-preferred expression of an operably linked nucleotide sequence.

16. An expression cassette comprising the promoter of claim 15.

17. An expression vector comprising the expression cassette of claim 16.

18. A plant having stably incorporated into its genome an expression cassette comprising a promoter operably linked to a nucleotide sequence, wherein said promoter is the promoter of claim 15.

19. Seed of the plant of claim 18, said seed comprising said expression cassette.

20. A method for expressing a nucleotide sequence in a plant, said method comprising, stably incorporating into the genome of a plant cell an expression cassette comprising a promoter operably linked to a nucleotide sequence, wherein said promoter is the promoter of claim 15.

21. The method of claim 20, wherein said nucleotide sequence is selectively expressed in the root.

22. A plant cell having stably incorporated into its genome an expression cassette comprising a promoter operably linked to a nucleotide sequence, wherein said promoter is the promoter of claim 15.

* * * * *

SEQUENCE LISTING

```
<160> NUMBER OF SEQ ID NOS: 1

<210> SEQ ID NO 1
<211> LENGTH: 4315
<212> TYPE: DNA
<213> ORGANISM: Zea Mays
<220> FEATURE:
<221> NAME/KEY: promoter
<222> LOCATION: (0)...(0)
<223> OTHER INFORMATION: knox1 promoter

<400> SEQUENCE: 1
tgcagccact cccattatgc acgcatagcg cacttgtgac ttgtgcaata aagtagtagt      60
acactagtac gtagctacta gcatgtagca ggtatagcta ggttgctcgg tcgagacttt     120
gagtgctacg catgcatcat gtcttcggat gaatcctgaa gaaaaaaaaa taagagcact     180
ggctttgtag taaatgtacc tctctctctc tctctctctc tttctctctc tctctctctc     240
tgaactctga agcacgagag cgaggagaga agcggcgatc agttagctga tcaccatttg     300
tttgtttgtt cagaattctg atgaccaata tgttcgttcg tttgtttatt cagaagtctg     360
ttggccactt gttctgtgtg tttgtgttcg aagccatgca tatatggctc gccgcggagg     420
cgtcatatat gatgtataca cacgtggagc gccggcgcag gtcaatcatc tgccggccag     480
ctgcccaggg ggatcaccgg ggagggaagg ctggcagtgc agggagggcg agggccgcgc     540
cgctatgggt gtacagcagg gtccgtccgc ccgcccgcgc ccgccgtggc gtgccgtgcg     600
gcggcaccga caggccgcgg tcgcaacagc tgtgggctgt gggcgtggcg ggggctggcg     660
cgcaccgcct cgctgtcgcg gaactccaac ggcggccaac cccaccccca acgcgtggcg     720
ggggctcaag ctgaaccacc gcgcgggctg ccgactgcgc gtgtggacca gccagccagc     780
```

-continued

```
cagccaaacc aaaccaaagc aaggcatggc aaccaccgga cccggctgct ctactcggtg    840
ccgcccgccg accgcgcgtg ccccgcctgg ggcctcttct cgcctccaca gcgtttgtac    900
tttgcggatt cggtcggtcg ctcgctcgct tctggttccg gtacacgtca ggactacctg    960
gattgctctg ctcatcagcc tcggctccgg ccgtccgtgc tcctcccatc ccttgctgct   1020
gctgctgctg cgttgcattg cattgcagct gtacatacag gaccacacat gcgacgtgtc   1080
ttgtcgtgtc gcggatgttc tctctgcgtc tgtacagtag caggcagccc acacccacag   1140
tgcggggcta gctttccagc tccgcaagga cacgtccccc tactgctgta caatgtacag   1200
tgcctcctca cgctgctaca agctaccgtc tccgtccgtg cggtagcagt agcagctccg   1260
atccgtccag cacagcaacc acacgtacgc tcgctcggtt tgcatgtgtt tgccgtgacc   1320
gtgaaggaca gccggttagt tctggccgcc tccgccgccg ccgcgggcg cccattctgc    1380 tgcaccgtcg ccattattct gctcagaaag gtccccgcct ctctcgtatc aggtcgcgct   1440
attatctctt atctagccgt accgcacact gacgcagcac aacactgctg gcttcggtct   1500
tttattatac tccctctgtt tcttttaat ttgtcgctgg attatgtaaa attgcactat    1560
ccagcgacaa ataaaagaa atggagggag tacaataata agcgaccttc gacaaaaaaa   1620
aaacaaaaac aaaaaagaac tcccattatt tcaatttcaa agggttacgg attttaata    1680 catttctcca tgtatgtaat cagacatcat gtatatctat gtatatagaa aaactaaaat   1740
agcttatgta atttagaatg aaagagtat aaccatggtg agtgtatgct cttagaatag    1800
tgctcggtca aattattttt atttttta taaatcagtt catacatata acaaaaaat      1860 tgatattat actttgcgga tatcgataaa acatcacgta gaactctatc gatcaagac    1920 acatcgataa aaaatctgtt ctttgcagat gcaaattgcg ttaaaccata ataatgaaga   1980
tttgtttggg taatcaatgg ttttcatgcc cctaacgaac ataataatga acattttttc   2040 gcccaccta gacggaggag gaagagaac caataatata tactagctcc atgatggatg    2100
gccgatggcg tgaacgactc atgcatgcat acatgaatga aaaatgtgg ggggtggccg    2160 caggactgat tatggccact gtacgaccga ctgtagggga tgaaagcctc gttgggtttg   2220
ttcaggtggc cgttcagcag tcaattctcc tcgctccata ttcttccata gaaacaacca   2280
ggaaaccgag tggaggagag ggagggagga tggaaggaga gagagccgtt gctggggcgt   2340
caggtgaaat cgagtggcct ccggttgccg gggaccatgc cattgccacc ggcccaccag   2400
caccagctag aagctagctc ggtgcaggca ggcgctgagc cagcgggaga gagagatgct   2460
atccaacatt ccaatccatc catatccaat accgatccta ttcctctccc cgctcgctcg   2520
cgcgccgcct ggcctgctgc tgcgctctgt agtctgtacg ctgctgcccc gcggcgcgcg   2580
tcgtccgccg atcgaggtga ccgcaagtac acgtactacg acagattcct gaccccaccc   2640
caaccgacga ctcgacgtct ccgacccatc tatctggccg gccgggtcgg ggtcgccggc   2700
cgtcgtggct ctcgcatgat tggttctctg acgatggacc cgatatatat cgacgttgcc   2760
tgccgggccc ttgttgttag cttgtgtcgc agcagattcg acgagagggg cggagctttg   2820
tgttatgtgg tgtcgctccg agaggcttcg gccaatagta aaagtacagc gcatttcagg   2880
acgaattata cggtatgttt ttttaaaaaa aatcagatac ataatgaaac gaacgaatac   2940 aatatttttac gcgtgcgtgg gcacgcgtaa ggaccggaaa atgtaggaga caagcaagca   3000
aaaaagagtg ctatattata ctaaaagttt tgatatatat atacatacat ataggcatac   3060
agccggcggc agcgtgtacg tcattgtccg tctgttacga tatgatcaga caaagcagct   3120
acagccggga cggcccgggc ccgccacggc gactacacgc acacggcggc ccaactaata   3180
```

-continued

```
ccaatatata taatactacg cctaaataat ccgatgcgat taacgcccac tgatgatgca    3240
tccttctaag ttctaatgct tccttaagta cgtagcttgc ctgccagcat ccagccacag    3300
ctgaagcctg aagggcagtc gatgtaaaag gcaagaataa tgcaggtcca ccgagacgac    3360
ggcggcggcg cggtgacgac gatgcaacag cagcagacgc ccgttccggg cgccaaccgc    3420
aaggttgcta gaggcaaccg aaggcgcccc cctcctcctg cttttttttt taaaaaaaaa    3480
aacccgccac cacccaaagt atttcttgaa accaactcct aattattcca tcgaattacc    3540
aaatgtatgt gcacctaacc tcctacagta tatcctaaag tttgtaccgc acttctacac    3600
catactcccc gcctactcat agtaggaaag gcattggtgc aactcttggt agctagctgt    3660
aggtactagg caccttgctc ttgctttagt tgttcctctt cctccttggg catgcttgga    3720
ttccaaagct tcaccaccct ccctcacctc cacttcctct ctctctctct ctctctctct    3780
ctctctctct ctctctctct ctctctcatt catctcgcct ttctttctta ccggccggcc    3840
ggccggcggc tgggctctgc aagtcaccca acttttctct gtttacacta cgatctcagg    3900
gctccggcga cgtgcggctc atcatcagat acaacctacc agctgctacc gtctcggtcg    3960
ccgcctagct ctccgcagcg gctagctcat ccggccggcc gccccttttc tcttgccgtt    4020
gcgcagttgc gccccttcc ccgcggctta ggaaccatcg aaaagacgcc tcaccatctc     4080
ctttgtgtcc ttgctaacta actcccccat taaatcctct ccttcctacc gcgctggccg    4140
tgtggtctct cagccctccg agttgatcca taagctagcg ccatcatcga tcgccatata    4200
tacatagcca aggacgcacg cgcgcgcgcg cgcaaaccag cgggagcgaa caccaaccgg    4260
ccggaccaat taagaagcag gctagcaagt cgaagaggaa agaagagaag ggggg         4315
```